United States Patent
Persson et al.

(10) Patent No.: US 6,905,683 B2
(45) Date of Patent: *Jun. 14, 2005

(54) HUMAN COAGULATION FACTOR VII VARIANTS

(75) Inventors: Egon Persson, Malmo (SE); Ole Hvilsted Olsen, Bronshoj (DK)

(73) Assignee: Novo Nordisk Healthcare A/G, Zurich (CH)

(*) Notice: Subject to any disclaimer, the term of this patent is extended or adjusted under 35 U.S.C. 154(b) by 202 days.

This patent is subject to a terminal disclaimer.

(21) Appl. No.: 09/848,107

(22) Filed: May 3, 2001

(65) Prior Publication Data
US 2003/0170863 A1 Sep. 11, 2003

Related U.S. Application Data

(60) Provisional application No. 60/204,712, filed on May 16, 2000, and provisional application No. 60/236,892, filed on Sep. 29, 2000.

(30) Foreign Application Priority Data

May 3, 2000 (DK) .................................. 2000 00734
Sep. 13, 2000 (DK) .................................. 2000 01360

(51) Int. Cl.⁷ .......................... A61K 35/14; A61K 38/48
(52) U.S. Cl. .................................. 424/94.63; 530/381
(58) Field of Search .......................... 435/69.1, 325; 514/2, 12; 530/350, 300, 381; 536/23.2; 424/94.63

(56) References Cited

U.S. PATENT DOCUMENTS

| | | | |
|---|---|---|---|
| 5,288,629 A | * | 2/1994 | Berkner ................ 435/352 |
| 5,580,560 A | | 12/1996 | Nicolaisen et al. |
| 5,874,407 A | | 2/1999 | Kelley et al. |
| 5,994,296 A | | 11/1999 | Ruf et al. |
| 2003/0096338 A1 | * | 5/2003 | Pedersen et al. ........ 435/69.1 |
| 2003/0130191 A1 | | 7/2003 | Persson et al. |
| 2003/0170863 A1 | | 9/2003 | Persson et al. |

FOREIGN PATENT DOCUMENTS

| | | |
|---|---|---|
| EP | 0 200 421 B1 | 12/1986 |
| JP | 10/59866 A | 3/1998 |
| JP | 2001 061479 | 8/1999 |
| WO | 88/10295 | 6/1987 |
| WO | 94/07515 | 10/1992 |
| WO | 94/27631 | 5/1994 |
| WO | 97/20939 | 11/1996 |
| WO | 98/31394 | 1/1998 |
| WO | 01/58935 A2 | 8/2001 |
| WO | 01/75086 A2 | 10/2001 |
| WO | 01/82943 A2 | 11/2001 |
| WO | 01/83725 A1 | 11/2001 |
| WO | 01/85198 A1 | 11/2001 |
| WO | 02/22776 A2 | 3/2002 |
| WO | 02/38162 A1 | 5/2002 |
| WO | 02/062376 A1 | 8/2002 |
| WO | 02/077218 A1 | 10/2002 |
| WO | 03/027147 A2 | 4/2003 |

OTHER PUBLICATIONS

Dictionary of Biochemistry and Molecular Biology (John Wiley & Sons, 2d ed. 1989).*
U.S. Appl. No. 60/184,036, filed Feb. 22, 2000.
Neuenschwander et al., Biochemistry, vol. 34, pp. 8701–8707 (1995).
Bernardi et al., Human Mutation, vol. 8, pp. 108–115 (1996).
Chang et al., Biochemistry, vol. 38, pp. 10940–10948 (1999).
Leonard et al., Abstract 1474, Journ of Int Soc Thromb and Haemost., p. 466 (Suppl. Aug. 1999).
Iakhiev et al., Thromb and Haemost, vol. 85 (3), pp. 458–463 (2001).
Jin et al., Journ of Mol Bio, vol. 307 (part 5), pp. 1503–1517.
Persson et al., Journ of Biol Chem, vol. 276 (31), pp. 29195–29199 (2001).
Peyvandi et al., Throm Haemost, vol. 84, pp. 250–257 (2000).
Peyvandi et al., Throm Haemost, vol. 88, pp. 750–755 (2002).

(Continued)

*Primary Examiner*—Jon Weber
*Assistant Examiner*—Sheridan Snedden
(74) *Attorney, Agent, or Firm*—Reza Green; Len S. Smith; Richard Bork

(57) ABSTRACT

The invention concerns novel coagulation factor VII variants, wherein the Leu residue in position 305 or the Phe residue in position 374 of SEQ ID NO 1 has been replaced by another amino acid residue which can be encoded by nucleic acid constructs and, optionally, wherein at least one other amino acid residue in the remaining positions in the protease domain has been replaced by another amino acid residue which can be encoded by nucleic acid constructs; with the proviso that the variant is not FVII(Ala305).

The invention further concerns nucleic acids encoding the Factor VII variants; vectors and cells comprising the nucleic acid; methods for producing the variants; pharmaceutical compositions comprising a Factor VII variant wherein the Leu residue in position 305 or the Phe residue in position 374 of SEQ ID NO 1 has been replaced by another amino acid residue which can be encoded by nucleic acid constructs and, optionally, wherein at least one other amino acid residue in the remaining positions in the protease domain has been replaced by another amino acid residue which can be encoded by nucleic acid constructs; use of the variants for producing a medicament for treatment or prophylaxis of bleeding disorders or enhancement of the coagulation system; and methods of treatment.

19 Claims, 3 Drawing Sheets

OTHER PUBLICATIONS

Soejima et al., Jorun of Bio Chem, vol. 276 (20), pp. 17229–17235 (2001).
U.S. Appl. No. 10/415,963, filed May 5, 2003, Ruf et al.
Dickinson et al., Biochemistry, vol. 93, pp. 14379–14384 (1996).
Abstract of Mizuguchi et al., Journal of the International Society on Thrombosis and Haemostasis, p. 466 (Supplement 1999).

Abstract of Jianping Jin, Ph.D., Dissertation Abstracts International, vol. 60, No. 12–B, p. 5929 (1999).

Abstract of Kumar A. Fair, D.S., European Journal of Biochemistry (Germany), vol. 217, No. 2, pp. 509–518 (1993).

* cited by examiner

FIGURE 1 - the amino acid sequence of native human coagulation Factor VII

```
Ala-Asn-Ala-Phe-Leu-GLA-GLA-Leu-Arg-Pro-Gly-Ser-Leu-GLA-Arg-GLA-Cys-Lys-
              5                  10                  15

GLA-GLA-Gln-Cys-Ser-Phe-GLA-GLA-Ala-Arg-GLA-Ile-Phe-Lys-Asp-Ala-GLA-Arg-
    20                  25                  30                  35

Thr-Lys-Leu-Phe-Trp-Ile-Ser-Tyr-Ser-Asp-Gly-Asp-Gln-Cys-Ala-Ser-Ser-Pro-
            40                  45                  50

Cys-Gln-Asn-Gly-Gly-Ser-Cys-Lys-Asp-Gln-Leu-Gln-Ser-Tyr-Ile-Cys-Phe-Cys-
 55              60                  65                  70

Leu-Pro-Ala-Phe-Glu-Gly-Arg-Asn-Cys-Glu-Thr-His-Lys-Asp-Asp-Gln-Leu-Ile-
        75                  80                  85                  90

Cys-Val-Asn-Glu-Asn-Gly-Gly-Cys-Glu-Gln-Tyr-Cys-Ser-Asp-His-Thr-Gly-Thr-
                95                  100                 105

Lys-Arg-Ser-Cys-Arg-Cys-His-Glu-Gly-Tyr-Ser-Leu-Leu-Ala-Asp-Gly-Val-Ser-
    110                 115                 120                 125

Cys-Thr-Pro-Thr-Val-Glu-Tyr-Pro-Cys-Gly-Lys-Ile-Pro-Ile-Leu-Glu-Lys-Arg-
            130                 135                 140

Asn-Ala-Ser-Lys-Pro-Gln-Gly-Arg-Ile-Val-Gly-Gly-Lys-Val-Cys-Pro-Lys-Gly-
145                 150                 155                 160

Glu-Cys-Pro-Trp-Gln-Val-Leu-Leu-Leu-Val-Asn-Gly-Ala-Gln-Leu-Cys-Gly-Gly-
        165                 170                 175                 180

Thr-Leu-Ile-Asn-Thr-Ile-Trp-Val-Val-Ser-Ala-Ala-His-Cys-Phe-Asp-Lys-Ile-
                185                 190                 195
```

Fig. 1

Lys-Asn-Trp-Arg-Asn-Leu-Ile-Ala-Val-Leu-Gly-Glu-His-Asp-Leu-Ser-Glu-His-
          200                205                210                215

Asp-Gly-Asp-Glu-Gln-Ser-Arg-Arg-Val-Ala-Gln-Val-Ile-Ile-Pro-Ser-Thr-Tyr-
          220                225                230

Val-Pro-Gly-Thr-Thr-Asn-His-Asp-Ile-Ala-Leu-Leu-Arg-Leu-His-Gln-Pro-Val-
235                240                245                250

Val-Leu-Thr-Asp-His-Val-Val-Pro-Leu-Cys-Leu-Pro-Glu-Arg-Thr-Phe-Ser-Glu-
          255                260                265                270

Arg-Thr-Leu-Ala-Phe-Val-Arg-Phe-Ser-Leu-Val-Ser-Gly-Trp-Gly-Gln-Leu-Leu-
                275                280                285

Asp-Arg-Gly-Ala-Thr-Ala-Leu-Glu-Leu-Met-Val-Leu-Asn-Val-Pro-Arg-Leu-Met-
          290                295                300                305 306

Thr-Gln-Asp-Cys-Leu-Gln-Gln-Ser-Arg-Lys-Val-Gly-Asp-Ser-Pro-Asn-Ile-Thr-
              310                315                320

Glu-Tyr-Met-Phe-Cys-Ala-Gly-Tyr-Ser-Asp-Gly-Ser-Lys-Asp-Ser-Cys-Lys-Gly-
325                330                335                340

Asp-Ser-Gly-Gly-Pro-His-Ala-Thr-His-Tyr-Arg-Gly-Thr-Trp-Tyr-Leu-Thr-Gly-
          345                350                355                360

Ile-Val-Ser-Trp-Gly-Gln-Gly-Cys-Ala-Thr-Val-Gly-His-Phe-Gly-Val-Tyr-Thr-
                365                370                375

Arg-Val-Ser-Gln-Tyr-Ile-Glu-Trp-Leu-Gln-Lys-Leu-Met-Arg-Ser-Glu-Pro-Arg-
          380                385                390                395

Pro-Gly-Val-Leu-Leu-Arg-Ala-Pro-Phe-Pro
          400                405 406

Fig. 1 (continued)

FIGURE 2 - the amino acid sequence of residues 300-322 in human coagulation factor VII and the corresponding regions of trypsin, thrombin and factor Xa.

```
              300                 305                 310
Factor VII   Leu-Asn-Val-Pro-Arg-Leu-Met-Thr-Gln-Asp-Cys-Leu-Gln-Gln-Ser
Trypsin      Leu-Lys-Ala-Pro-Ile-Leu-Asp-Asn-Ser-Ser-Cys-Lys-Ser--------
Thrombin     Val-Asn-Leu-Pro-Ile-Val-Glu-Arg-Pro-Val-Cys-Lys-Asp--------
Factor Xa    Leu-Glu-Val-Pro-Tyr-Val-Asp-Arg-Asn-Ser-Cys-Lys-Leu--------

315                 320
Factor VII   Arg-Lys-Val-Gly-Asp-Ser-Pro-Asn
Trypsin      ------------Ala-Tyr-Pro-Gly-Gln
Thrombin     ------------Ser-Thr-Arg-Ile-Arg
Factor Xa    ------------Ser-Ser-Ser-Phe-Ile
```

Fig. 2

HUMAN COAGULATION FACTOR VII VARIANTS

CROSS REFERENCE TO RELATED APPLICATIONS

This application claims priority under 35 U.S.C. 119 of Danish application no. PA 2000 00734 filed on May 3, 2000, Danish application no. PA 2000 01360 filed on Sep. 13, 2000, U.S. provisional application No. 60/204,712 filed on May 16, 2000, and U.S. provisional application No. 60/236,892 filed on Sep. 29, 2000, the contents of which are fully incorporated herein by reference.

FIELD OF THE INVENTION

The present invention relates to novel human coagulation Factor VIIa variants having coagulant activity as well as nucleic acid constructs encoding such variants, vectors and host cells comprising and expressing the nucleic acid, pharmaceutical compositions, uses and methods of treatment.

BACKGROUND OF THE INVENTION

Blood coagulation is a process consisting of a complex interaction of various blood components (or factors) that eventually gives raise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot. In recent years Factor VII and tissue factor have been found to be the main initiators of blood coagulation.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. Like several other plasma proteins involved in haemostasis, Factor VII is dependent on Vitamin K for its activity, which is required for the gamma-carboxylation of multiple glutamic acid residues that are clustered close to the amino terminus of the protein. These gamma-carboxylated glutamic acids are required for the metal ion-induced interaction of Factor VII with phospholipids. The conversion of zymogen Factor VII into the activated two-chain molecule occurs by cleavage of an internal $Arg_{152}$-$Ile_{153}$ peptide bond. In the presence of tissue factor, phospholipids and calcium ions, the two-chain Factor VIIa rapidly activates Factor X or Factor IX by limited proteolysis.

It is often desirable to stimulate or improve the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease. Bleeding is also a major problem in connection with surgery and other forms of tissue damage.

European Patent No. 200,421 (ZymoGenetics) relates to the nucleotide sequence encoding human Factor VII and the recombinant expression of Factor VII in mammalian cells.

Dickinson et al. (Proc. Natl. Acad. Sci. USA (1996) 93, 14379–14384) relates to a Factor VII variant wherein Leu305 has been replaced by Ala (FVII(Ala305)).

Iwanaga et al. (Thromb. Haemost. (supplement August 1999), 466, abstract 1474) relates to Factor VIIa variants wherein residues 316–320 are deleted or residues 311–322 are replaced with the corresponding residues from trypsin.

There is, however, still a need for variants of Factor VIIa having coagulant activity, variants with high activity that can be administered at relatively low doses, and variants which do not produce the undesirable side effects such as systemic activation of the coagulation system and bleeding, respectively, associated with conventional therapies.

SUMMARY OF THE INVENTION

The invention provides coagulation Factor VIIa variants with coagulant activity. In a first aspect, the invention provides a human coagulation Factor VII variant, wherein the Leu residue in position 305 or the Phe residue in position 374 of SEQ ID NO 1 has been replaced by another amino acid residue which can be encoded by nucleic acid constructs and, optionally, wherein at least one other amino acid residue in the remaining positions in the protease domain has been replaced by another amino acid residue which can be encoded by nucleic acid constructs; with the proviso that the variant is not FVII(Ala305).

In one embodiment, the Leu residue in position 305 or the Phe residue in position 374 of SEQ ID NO 1 and at the most 20 amino acid residues in the remaining positions in the protease domain (positions 153–406) have been replaced. In one embodiment, at the most 15 additional amino acid residues are replaced; in another embodiment, at the most 10 amino acid residues are replaced; in another embodiment, at the most 5 amino acid residues are replaced.

In another embodiment of the invention the Leu residue in position 305 or the Phe residue in position 374 of SEQ ID NO 1 and at least one residue in position 274 and/or 300–304 and/or position 306–312 have been replaced.

In another embodiment, the Leu residue in position 305 or the Phe residue in position 374 of SEQ ID NO 1 and at least the residue in position 274 have been replaced.

In another embodiment, the Leu residue in position 305 or the Phe residue in position 374 of SEQ ID NO 1 and at least one residue in position 300–304 have been replaced.

In another embodiment, the Leu residue in position 305 or the Phe residue in position 374 of SEQ ID NO 1 and at least one residue in position 306–312 have been replaced.

In another embodiment, the Ala residue in position 274 has been replaced by Met or Leu or Lys or Arg; and/or the Arg residue in position 304 has been replaced by Tyr or Phe or Leu or Met; and/or the Met residue in position 306 has been replaced by Asp or Asn; and/or the Asp residue in position 309 has been replaced by Ser or Thr.

In another embodiment, the Leu residue in position 305 or the Phe residue in position 374 is the only amino acid residue that has been replaced.

In one embodiment, the Leu residue in position 305 has been replaced. In another embodiment, the Phe residue in position 374 has been replaced.

In one embodiment, the Phe residue in position 374 is the only amino acid residue that has been replaced.

In another embodiment, the Leu residue in position 305 is the only amino acid residue that has been replaced.

In a specific embodiment, the Leu residue in position 305 has been replaced by Val.

In another embodiment, the Leu residue in position 305 has been replaced by an amino acid residue selected from the group consisting of Val, Tyr and Ile, or the Phe residue in position 374 has been replaced by Pro.

In one embodiment of the invention the residues 300–322, 305–322, 300–312, or 305–312 of SEQ ID NO 1 are replaced by the corresponding sequences from trypsin (SEQ ID NOS 3,7,11,15, respectively), thrombin (SEQ ID NOS 4,8,12,16, respectively), Factor Xa (SEQ ID NO 5,9,13,17, respectively) or another constitutively active serine protease. In yet another embodiment, one or more of residues 313–322 of SEQ ID NO 1 is/are deleted.

In one aspect, the amino acid residue at position 305 has been replaced by an amino acid residue selected from a list of Ala, Val, Ile, Met, Phe, Trp, Pro, Gly, Ser, Thr, Cys, Tyr, Asn, Glu, Lys, Arg, His, Asp and Gln, or the amino acid residue at position 374 has been replaced by an amino acid residue selected from a list of Ala, Val, Leu, Ile, Met, Trp, Pro, Gly, Ser, Thr, Cys, Tyr, Asn, Glu, Lys, Arg, His, Asp or Gln, with the proviso that the variant is not FVII(Ala305).

In another aspect, the amino acid residue at position 305 has been replaced by an amino acid residue selected from a list of Ala, Val, Ile, Met, Phe, Trp, Pro, Gly, Ser, Thr, Cys, Tyr, Asn, Glu, Lys, Arg, His, Asp and Gln, or the amino acid residue at position 374 has been replaced by an amino acid residue selected from a list of Ala, Val, Leu, Ile, Met, Trp, Pro, Gly, Ser, Thr, Cys, Tyr, Asn, Glu, Lys, Arg, His, Asp or Gln.

In another aspect, the amino acid residue at position 305 has been replaced by an amino acid residue that can be encoded by nucleic acids, such as Ala, Val, Ile, Met, Phe, Trp, Pro, Gly, Ser, Thr, Cys, Tyr, Asn, Glu, Lys, Arg, His, Asp and Gln, and the amino acid residue at position 374 has been replaced by an amino acid residue that can be encoded by nucleic acid, such as Ala, Val, Leu, Ile, Met, Trp, Pro, Gly, Ser, Thr, Cys, Tyr, Asn, Glu, Lys, Arg, His, Asp or Gln.

In one embodiment, the amino acid residue at position 305 has been replaced by an amino acid residue selected from a list of Ala, Val, Ile, Met, Phe, Trp, Pro, Gly, Ser, Thr, Cys, Tyr, Asn, Glu, Lys, Arg, His, Asp and Gln, and the amino acid residue at position 374 has been replaced by an amino acid residue selected from a list of Ala, Val, Leu, Ile, Met, Trp, Pro, Gly, Ser, Thr, Cys, Tyr, Asn, Glu, Lys, Arg, His, Asp or Gln.

The present invention also provides a human coagulation Factor VII variant, wherein the ratio between the activity of the variant and the activity of the native Factor VII polypeptide shown in SEQ ID NO 1 is at least about 1.25 when tested in the "In Vitro Hydrolysis Assay" defined herein. In one embodiment, the ratio is at least about 2.0; in yet another embodiment, at least about 4.0.

In another aspect, the invention provides human coagulation Factor VIIa variants that have increased tissue factor-independent activity compared to native human coagulation Factor VIIa. In another aspect, the increased activity is not accompanied by changes in the substrate specificity. In another aspect of the invention, the binding of the variants to tissue factor should not be impaired and the variants should have at least the activity of wild-type Factor VIIa when bound to tissue factor.

Another aspect of the present invention relates to a nucleic acid construct, preferably a DNA construct, comprising a nucleotide sequence encoding a Factor VII variant according to the invention.

In another aspect, the invention provides a recombinant vector comprising the nucleic acid construct.

Another aspect of the present invention relates to a recombinant host cell, preferably of mammalian origin, comprising the nucleic acid construct or the recombinant vector.

In one embodiment, the recombinant host cells are CHO or BHK cells.

Another aspect of the present invention relates to a transgenic animal or a transgenic plant containing and expressing the nucleic acid construct.

Other aspects of the present invention relate to a pharmaceutical composition comprising a human coagulation Factor VII variant wherein the Leu residue in position 305 or the Phe residue in position 374 of SEQ ID NO 1 has been replaced by another amino acid residue which can be encoded by nucleic acid constructs and, optionally, wherein at least one other amino acid residue in the remaining positions in the protease domain has been replaced by another amino acid residue which can be encoded by nucleic acid constructs, optionally in combination with a pharmaceutically acceptable carrier; to the human coagulation Factor VII variant for use as a medicament; to the use of the human coagulation Factor VII variant for the preparation of a composition for the treatment or prophylaxis of bleeding episodes or for the enhancement of the normal haemostatic system; to a method for the treatment or prophylaxis of bleeding episodes in a subject or for the enhancement of the normal haemostatic system; and to methods for producing a Factor VII variant according to the invention.

BRIEF DESCRIPTION OF THE DRAWINGS

FIG. 1 shows the full amino acid sequence of native human coagulation Factor VII (SEQ ID NO 1).

FIG. 2 shows the region 300–322 of human coagulation Factor VII and the corresponding region of homologous serine proteases:
Region 300–322 of Factor VII (SEQ ID NO 2)
Corresponding region of trypsin (SEQ ID NO 3)
Corresponding region of thrombin (SEQ ID NO 4)
Corresponding region of FXa (SEQ ID NO 5)
Region 305–322 of Factor VII (SEQ ID NO 6)
Corresponding region of trypsin (SEQ ID NO 7)
Corresponding region of thrombin (SEQ ID NO 8)
Corresponding region of FXa (SEQ ID NO 9)
Region 300–312 of Factor VII (SEQ ID NO 10)
Corresponding region of trypsin (SEQ ID NO 11)
Corresponding region of thrombin (SEQ ID NO 12)
Corresponding region of FXa (SEQ ID NO 13)
Region 305–312 of Factor VII (SEQ ID NO 14)

Corresponding region of trypsin (SEQ ID NO 15)
Corresponding region of thrombin (SEQ ID NO 16)
Corresponding region of FXa (SEQ ID NO 17)

DETAILED DESCRIPTION OF THE INVENTION

It has now been found that Factor VIIa variants wherein at least one of the amino acid residues Leu305 or Phe374 (and optionally one or more additional residues) is/are replaced by another amino acid residue have coagulant activity.

The residues Leu305 and Phe374 are located at each end of an α-helix starting at residue 307. This α-helix is found in the tissue factor-complexed form of Factor VIIa. In free Factor VIIa (Factor VIIa not bound to tissue factor) the helix is distorted and thus possibly unstable. The helix is believed to be important to the activity. The variants according to the present invention attain the active conformation, which normally has to be induced by tissue factor.

The activity may be due to a stabilisation of the a-helix starting at residue 307, a reorientation of the helix or some other change in conformation. Replacement of one of the residues Leu305 or Phe374, which are located at each end of the helix, will induce a reorientation and/or stabilisation of the helix.

Due to the higher inherent activity of the described Factor VIIa variant compared to native Factor VIIa, a lower dose will be adequate to obtain a functionally adequate concentration at the site of action and thus it will be possible to administer a lower dose to the subject having bleeding episodes or needing enhancement of the normal haemostatic system.

As discussed briefly above, it has been found by the present inventors that by replacing either the Leu residue in position 305 or the Phe residue in position 374 with another amino acid, Factor VIIa will spontaneously attain a more active conformation that normally has to be induced by tissue factor. Examples of preferred amino acid residues, which may replace Leu in position 305, include Val, Tyr and Ile.

Thus, it is contemplated by the present inventors that such Factor VIIa variants exhibit an inherent activity which may be therapeutically useful in situations where the procoagulant activity is independent of tissue factor (Factor Xa generation on the platelet surface) such as when high doses of, for example, NovoSeven® are administered.

As said, replacement of other amino acid residues in the sequence may, in addition to the effect obtained by replacement of the Leu305 or the Phe374 residue, further facilitate formation of the active conformation of the molecule. In principle these remaining positions may be anywhere (except, of course, in position 305 or 374) in the protease domain. It is believed, however, that the most pronounced effects will be seen when the above-mentioned mutations are carried out in the vicinity (sequential or three-dimensional) of residue 305 (or 374).

It is well established that replacement of a few amino acid residues in the N-terminal Gla domain (residues 1–37) of Factor VII can provide the protein with a substantially higher affinity for membrane phospholipids, such as membrane phospholipids of tissue factor-bearing cells or of platelets, thereby generating Factor VII derivatives which have an improved procoagulant effect.

Thus, the Factor VII variants mentioned above may, in addition to the already performed amino acid replacement in positions 305 or 374 and the optional amino acid replacements in positions 274, 300–304 and 306–310 or elsewhere in the protease domain, also have some amino acid residues replaced in the N-terminal Gla domain, thereby obtaining a protein having an increased activity as well as an increased affinity for membrane phospholipids compared to native Factor VII.

Preferably the amino acid residues in positions 10 and 32 (referring to SEQ ID NO 1) of Factor VII may be replaced with another amino acid residue that can be encoded by nucleic acid constructs.

Examples of preferred amino acid residues to be incorporated in the above-mentioned positions are:

The amino acid residue Pro in position 10 is replaced by Gln, Arg, His, Gln, Asn or Lys; and/or the amino acid residue Lys in position 32 is replaced by Glu, Gln or Asn.

Other residues in the Gla domain, based on the different phospholipid affinities and sequences of the vitamin K-dependent plasma proteins, may also be considered for substitution.

In the present context the three-letter or one-letter indications of the amino acids have been used in their conventional meaning as indicated in table 1. Unless indicated explicitly, the amino acids mentioned herein are L-amino acids. Further, the left and right ends of an amino acid sequence of a peptide are, respectively, the N- and C-termini unless otherwise specified.

TABLE 1

Abbreviations for amino acids:

| Amino acid | Three-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |

The term "N-terminal GLA-domain" means the amino acid sequence 1–37 of Factor VII.

The term "protease domain" means the amino acid sequence 153–406 of Factor VII (the heavy-chain of Factor VIIa).

The three-letter indication "GLA" means 4-carboxyglutamic acid (γ-carboxyglutamate).

The indication "FVII(Ala305)" means Factor VII as shown in SEQ ID NO 1 wherein the Leu residue in position 305 has been replaced by Ala.

The term "Factor VII" or "FVII" as used herein is intended to comprise the inactive one-chain zymogen Factor VII molecule as well as the activated two-chain Factor VII molecule, and may, where appropriate, be used interchangeably with the terms "polypeptide", "protein", "protease" and "enzyme".

As used herein the term "nucleic acid construct" is intended to mean any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding the polypeptide of interest. The construct may optionally contain other nucleic acid segments. In a similar way, the term "amino acid residue which can be encoded by nucleic acid constructs" covers amino acid residues which can be encoded by the nucleic acid constructs defined above, i.e. amino acids such as Ala, Val, Leu, Ile, Met, Phe, Trp, Pro, Gly, Ser, Thr, Cys, Tyr, Asn, Glu, Lys, Arg, His, Asp and Gln.

In the present context, the term "treatment" is meant to include both prevention of an expected bleeding, such as in surgery, and regulation of an already occurring bleeding, such as in trauma, with the purpose of inhibiting or minimising the bleeding. Prophylactic administration of the Factor VIIa variant according to the invention is thus included in the term "treatment".

The term "activity" means the ability to generate thrombin, the term "inherent activity" also includes the ability to generate thrombin on the surface of activated platelets in the absence of tissue factor.

The term "enhancement of the normal haemostatic system" means an enhancement of the ability to generate thrombin.

As used herein the term "bleeding disorder" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

The term "bleeding episodes" is meant to include uncontrolled and excessive bleeding which is a major problem both in connection with surgery and other forms of tissue damage. Uncontrolled and excessive bleeding may occur in subjects having a normal coagulation system and subjects having coagulation or bleeding disorders. Clotting factor deficiencies (haemophilia A and B, deficiency of coagulation factors XI or VII) or clotting factor inhibitors may be the cause of bleeding disorders. Excessive bleedings also occur in subjects with a normally functioning blood clotting cascade (no clotting factor deficiencies or -inhibitors against any of the coagulation factors) and may be caused by a defective platelet function, thrombocytopenia or von Willebrand's disease. In such cases, the bleedings may be likened to those bleedings caused by haemophilia because the haemostatic system, as in haemophilia, lacks or has abnormal essential clotting "compounds" (such as platelets or von Willebrand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with haemophilia. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient".

As used herein the term "appropriate growth medium" means a medium containing nutrients and other components required for the growth of cells and the expression of the nucleic acid sequence encoding the Factor VII variant of the invention.

Preparation of Factor VII Variants

The Factor VII variants described herein may be produced by means of recombinant nucleic acid techniques. In general, a cloned wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells. The complete nucleotide and amino acid sequences for human Factor VII are known (see U.S. Pat. No. 4,784,950, where the cloning and expression of recombinant human Factor VII is described). The bovine Factor VII sequence is described in Takeya et al., *J. Biol. Chem.* 263:14868–14872 (1988)).

The amino acid sequence alterations may be accomplished by a variety of techniques. Modification of the nucleic acid sequence may be by site-specific mutagenesis. Techniques for site-specific mutagenesis are well known in the art and are described in, for example, Zoller and Smith (*DNA* 3:479–488, 1984) or "Splicing by extension overlap", Horton et al., *Gene* 77, 1989, pp. 61–68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. *PCR Protocols*, 1990, Academic Press, San Diego, Calif., USA).

The nucleic acid construct encoding the Factor VII variant of the invention may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., *Molecular Cloning: A Laboratory Manual*, 2nd. Ed. Cold Spring Harbor Laboratory, Cold Spring Harbor, N.Y., 1989).

The nucleic acid construct encoding the Factor VII variant may also be prepared synthetically by established standard methods, e.g. the phosphoamidite method described by Beaucage and Caruthers, *Tetrahedron Letters* 22 (1981), 1859–1869, or the method described by Matthes et al., *EMBO Journal* 3 (1984), 801–805. According to the phosphoamidite method, oligonucleotides are synthesised, e.g. in an automatic DNA synthesiser, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct,

DNA sequences for use in producing Factor VII variants according to the present invention will typically encode a pre-pro polypeptide at the amino-terminus of Factor VII to obtain proper posttranslational processing (e.g. gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the Factor VII variants where those modifications do not significantly impair the ability of the protein to act as a coagulant. For example, the Factor VII variants can also be modified in the activation cleavage site to inhibit the conversion of zymogen Factor VII into its activated two-chain form, as generally described in U.S. Pat. No. 5,288,629.

Expression vectors for use in expressing Factor VIIa variants will comprise a promoter capable of directing the transcription of a cloned gene or cDNA. Preferred promoters for use in cultured mammalian cells include viral promoters and cellular promoters. Viral promoters include the SV40 promoter (Subramani et al., *Mol. Cell. Biol.* 1:854–864, 1981) and the CMV promoter (Boshart et al., *Cell* 41:521–530, 1985). A particularly preferred viral promoter is the major late promoter from adenovirus 2 (Kaufman and Sharp, *Mol. Cell. Biol.* 2:1304–1319, 1982). Cellular promoters include the mouse kappa gene promoter (Bergman et al., *Proc. Natl. Acad. Sci. USA* 81:7041–7045, 1983) and the mouse $V_H$ promoter (Loh et al., *Cell* 33:85–93, 1983). A particularly preferred cellular promoter is the mouse metallothionein-I promoter (Palmiter et al., *Science* 222:809–814, 1983). Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nucl. Acids Res.* 9:3719–3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

Cloned DNA sequences are introduced into cultured mammalian cells by, for example, calcium phosphate-mediated transfection (Wigler et al., *Cell* 14:725–732, 1978; Corsaro and Pearson, *Somatic Cell Genetics* 7:603–616, 1981; Graham and Van der Eb, *Virology* 52d:456–467, 1973) or electroporation (Neumann et al., *EMBO J.* 1:841–845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers are reviewed by Thilly (*Mammalian Cell Technology*, Butterworth Publishers, Stoneham, Mass., incorporated herein by reference). The person skilled in the art will easily be able to choose suitable selectable markers.

Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically for 1–2 days, to begin expressing the gene of interest. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, *More Gene Manipulations in Fungi*, Academic Press, CA, 1991). Growth media generally include a carbon source, a nitrogen source, essential amino acids, essential sugars, vitamins, salts, phospholipids, proteins and growth factors. For production of gamma-carboxylated Factor VII variants, the medium will contain vitamin K, preferably at a concentration of about 0.1 mg/ml to about 5 mg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the desired Factor VII variant.

Preferred mammalian cell lines include the CHO (ATCC CCL 61), COS-1 (ATCC CRL 1650), baby hamster kidney (BHK) and 293 (ATCC CRL 1573; Graham et al., *J. Gen. Virol.* 36:59–72, 1977) cell lines. A preferred BHK cell line is the tk⁻ ts13 BHK cell line (Waechter and Baserga, *Proc. Natl. Acad. Sci. USA* 79:1106–1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216–4220, 1980).

Transgenic animal technology may be employed to produce the Factor VII variants of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene (see Whitelaw et al., *Biochem. J.* 286: 31–39 (1992)). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836–840 (1988); Palmiter et al., *Proc. Natl. Acad. Sci. USA* 88: 478–482 (1991); Whitelaw et al., *Transgenic Res.* 1: 3–13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment that provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the variant Factor VII sequence is replaced with corresponding sequences from a milk specific protein gene. Such replacement provides a putative tissue-specific initiation environment to enhance expression. It is convenient to replace the entire variant Factor VII pre-pro and 5' non-coding sequences with those of, for example, the BLG gene, although smaller regions may be replaced.

For expression of Factor VII variants in transgenic animals, a DNA segment encoding variant Factor VII is operably linked to additional DNA segments required for its expression to produce expression units. Such additional segments include the above-mentioned promoter, as well as sequences that provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein (see, for example, von Heijne, *Nucl. Acids Res.* 14: 4683–4690 (1986); and Meade et al., U.S. Pat. No. 4,873,316, which are incorporated herein by reference).

Construction of expression units for use in transgenic animals is conveniently carried out by inserting a variant Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a variant Factor VII polypeptide; thereby creating a gene fusion that includes the expression control sequences of the milk protein gene. In any event, cloning of the expression units in plasmids or other vectors facilitates the amplification of the variant Factor VII sequence. Amplification is conveniently carried out in bacterial (e.g. *E. coli*) host cells, thus the vectors will typically include an origin of replication and a selectable marker functional in bacterial host cells. The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468–1474 (1988)) or site-directed integration using embryonic stem (ES) cells (reviewed by Bradley et al., *Bio/Technology* 10: 534–539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., *Bio/Technology* 6: 179–183 (1988); Wall et al., *Biol. Reprod.* 32: 645–651 (1985); Buhler et al., *Bio/Technology* 8: 140–143 (1990); Ebert et al., Bio/Technology 9: 835–838 (1991); Krimpenfort et al., *Bio/Technology* 9: 844–847 (1991); Wall et al., *J. Cell. Biochem.* 49: 113–120 (1992); U.S. Pat. Nos. 4,873,191; 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., *Proc. Natl. Acad. Sci. USA* 77: 7380–7384 (1980); Gordon and Ruddle, *Science* 214: 1244–1246 (1981); Palmiter and Brinster, *Cell* 41: 343–345 (1985); Brinster et al., *Proc. Natl. Acad. Sci. USA* 82: 4438–4442 (1985); and Hogan et al. (ibid.)). These techniques were subsequently adapted for use with larger animals, including livestock species (see, e.g., WO 88/00239, WO 90/05188, and WO 92/11757; and Simons et al., *Bio/Technology* 6: 179–183 (1988)). To summarise, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed.

Production in transgenic plants may also be employed. Expression may be generalised or directed to a particular organ, such as a tuber (see, Hiatt, *Nature* 344:469–479 (1990); Edelbaum et al., *J. Interferon Res.* 12:449–453 (1992); Sijmons et al., *Bio/Technology* 8:217–221 (1990); and EP 0 255 378).

The Factor VII variants of the invention are recovered from cell culture medium or milk. The Factor VII variants of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). Preferably, they may be purified by affinity chromatography on an anti-Factor VII antibody column. The use of calcium-dependent monoclonal antibodies, as described by Wakabayashi et al., *J. Biol. Chem.* 261:11097–11108, (1986) and Thim et al., *Biochemistry* 27: 7785–7793, (1988), is particularly preferred. Additional purification may be achieved by conventional chemical purification means, such as high performance liquid chromatography. Other methods of purification, including barium citrate precipitation, are known in the art, and may be applied to the purification of the novel Factor VII variants described herein (see, for example, Scopes, R., *Protein Purification*, Springer-Verlag, N.Y., 1982).

For therapeutic purposes it is preferred that the Factor VII variants of the invention are substantially pure. Thus, in a preferred embodiment of the invention the Factor VII variants of the invention is purified to at least about 90 to 95% homogeneity, preferably to at least about 98% homogeneity. Purity may be assessed by e.g. gel electrophoresis and amino-terminal amino acid sequencing.

The Factor VII variant is cleaved at its activation site in order to convert it to its two-chain form. Activation may be carried out according to procedures known in the art, such as those disclosed by Osterud, et al., *Biochemistry* 11:2853–2857 (1972); Thomas, U.S. Pat. No. 4,456,591; Hedner and Kisiel, *J. Clin. Invest.* 71:1836–1841 (1983); or Kisiel and Fujikawa, *Behring Inst. Mitt.* 73:29–42 (1983). Alternatively, as described by Bjoern et al. (Research Disclosure, 269 September 1986, pp. 564–565), Factor VII may be activated by passing it through an ion-exchange chromatography column, such as Mono Q® (Pharmacia fine Chemicals) or the like. The resulting activated Factor VII variant may then be formulated and administered as described below.

Assays

The invention also provides suitable assays for selecting preferred Factor VIIa variants according to the invention. These assays can be performed as a simple preliminary in vitro test.

Thus, Example 6 herein discloses a simple test (entitled "In Vitro Hydrolysis Assay") for the activity of Factor VIIa variants of the invention. Based thereon, Factor VIIa variants which are of particular interest are such variants where the ratio between the activity of the variant and the activity of native Factor VII shown in FIG. 1 is above 1.0, e.g. at least about 1.25, preferably at least about 2.0, such as at least about 3.0 or, even more preferred, at least about 4.0 when tested in the "In Vitro Hydrolysis Assay" defined herein.

The activity of the variants can also be measured using a physiological substrate such as factor X (see Example 7), suitably at a concentration of 100–1000 nM, where the factor Xa generated is measured after the addition of a suitable chromogenic substrate (eg. S-2765). In addition, the activity assay may be run at physiological temperature.

The ability of the Factor VIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542–547 which is hereby incorporated as reference).

Administration and Pharmaceutical Compositions

The Factor VII variants according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant Factor VIIa because of a localised haemostatic process of the kind induced by the complex formation between Factor VIIa and TF exposed at the site of vessel wall injury. The Factor VII variants according to the invention may thus also be used in their activated form to control such excessive bleedings associated with a normal haemostatic mechanism.

For treatment in connection with deliberate interventions, the Factor VII variants of the invention will typically be administered within about 24 hours prior to performing the intervention, and for as much as 7 days or more thereafter. Administration as a coagulant can be by a variety of routes as described herein.

The dose of the Factor VII variants ranges from about 0.05 mg to 500 mg/day, preferably from about 1 mg to 200 mg/day, and more preferably from about 10 mg to about 175 mg/day for a 70 kg subject as loading and maintenance doses, depending on the weight of the subject and the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII variant of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII variants of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII variant in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the Factor VII variant. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

The compositions containing the Factor VII variants of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII variant per day for a 70 kg subject, with dosages of from about 1.0 mg to about 200 mg of the Factor VII variant per day being more commonly used.

It must be kept in mind that the materials of the present invention may generally be employed in serious disease or injury states, that is, life threatening or potentially life threatening situations. In such cases, in view of the minimisation of extraneous substances and general lack of immunogenicity of human Factor VII variants in humans, it is possible and may be felt desirable by the treating physician to administer a substantial excess of these variant Factor VII compositions.

In prophylactic applications, compositions containing the Factor VII variant of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII variants may be administered by continuous infusion using e.g. a portable pump system.

Local delivery of the Factor VII variant of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII variant sufficient to effectively treat the subject.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

The terminology for amino acid substitutions used in the following examples are as follows. The first letter represent the amino acid naturally present at a position of SEQ ID NO 1. The following number represent the position in SEQ ID NO 1. The second letter represent the different amino acid substituting for the natural amino acid. An example is [L305V]-FVII, where the leucine at position 305 of SEQ ID NO 1 is replaced by a valine. In another example, [L305V/M306D/D309S]-FVII, the leucine at position 305 of SEQ ID NO 1 is replaced by a valine and the methionine at position 306 of SEQ ID NO 1 is replaced by an aspartic acid and the aspartic acid at position 309 of SEQ ID NO 1 is replaced by a serine, all mutations in the same Factor VII polypeptide.

Example 1
DNA Encoding [L305V/M306D/D309S]-FVII, [L305V]-FVII, [L305I]-FVII, [L305T]-FVII and [F374P]-FVII.

DNA constructs encoding [L305V/M306D/D309S]-FVII, [L305V]-FVII, [L305I]-FVII, [L305T]-FVII and [F374P]-FVII were prepared by site-directed mutagenesis using a supercoiled, double stranded DNA vector with an insert of interest and two synthetic primers containing the desired mutation. The following primers were used:

```
For [L305V]-FVII:
5'-GGT GCC CCG GGT GAT GAC CCA GGA C-3'        (SEQ ID NO 18)

5'-GTC CTG GGT CAT CAC CCG GGG CAC G-3'        (SEQ ID NO 19)

For [M306D/D309S]-FVII:
5'-TCT AGA TAC CCA GTC TTG CCT GCA GCA GTC ACG GAA-3'  (SEQ ID NO 20)

5'-TTC CGT GAC TGC TGC AGG CAA GAC TGG GTA TCT AGA-3'  (SEQ ID NO 21)

For [F374P]-FVII:
5'-CCG TGG GCC ACC CTG GGG TGT ACA CC-3'       (SEQ ID NO 22)

5'-GGT GTA CAC CCC AGG GTG GCC CAC GG-3'       (SEQ ID NO 23)

For [L305I]-FVII:
5'-CCT CAA CGT GCC CCG GAT CAT GAC CCA GGA C-3' (SEQ ID NO 24)

5'-GTC CTG GGT CAT GAT CCG GGG CAC GTT GAG G-3' (SEQ ID NO 25)

For [L305T]-FVII:
5'-CCT CAA CGT GCC CCG GAC GAT GAC CCA GGA C-3' (SEQ ID NO 26)

5'-GTC CTG GGT CAT CGT CCG GGG CAC GTT GAG G-3' (SEQ ID NO 27)
```

The oligonucleotide primers, each complementary to opposite strands of the vector, were extended during temperature cycling by means of Pfu DNA polymerase. On incorporation of the primers, a mutated plasmid containing staggered nicks was generated. Following temperature cycling, the product was treated with DpnI which is specific for methylated and hemimethylated DNA to digest the parental DNA template and to select for mutation-containing synthesized DNA.

Procedures for preparing a DNA construct using polymerase chain reaction using specific primers are well known to persons skilled in the art (cf. *PCR Protocols*, 1990, Academic Press, San Diego, Calif., USA).

Example 2
Preparation of [L305V/M306D/D309S]-FVII.

BHK cells were transfected essentially as previously described (Thim et al. (1988) *Biochemistry* 27, 7785–7793; Persson and Nielsen (1996) *FEBS Lett.* 385, 241–243) to obtain expression of the variant [L305V/M306D/D309S]-FVII. The Factor VII variant was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 1 M NaCl, 5 mM $CaCl_2$, 0.1% Triton X-100, pH 7.5. The fractions containing [L305V/M306D/D309S]-FVII were pooled, 10 mM $CaCl_2$ was added, and applied to a 25-ml column containing monoclonal antibody F1A2 (Novo Nordisk, Bagsværd, Denmark) coupled to CNBr-activated Sepharose 4B (Pharmacia Biotech). The column was equilibrated with 50 mM Hepes, pH 7.5, containing 10 mM $CaCl_2$, 100 mM NaCl and 0.02% Triton X-100. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [L305V/M306D/D309S]-FVII was transferred to a $Ca^{2+}$-containing buffer. The yield of each step was followed by factor VII ELISA measurements and the purified protein was analysed by SDS-PAGE.

Example 3
Preparation of [L305V]-FVII.

BHK cells were transfected essentially as previously described (Thim et al. (1988) *Biochemistry* 27, 7785–7793; Persson and Nielsen (1996) *FEBS Lett.* 385, 241–243) to obtain expression of the variant [L305V]-FVII. The Factor VII variant was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 1 M NaCl, 5 mM $CaCl_2$, 0.1% Triton X-100, pH 7.5. The fractions containing [L305V]-FVII were pooled, 10 mM $CaCl_2$ was added, and applied to a 25-ml column containing monoclonal antibody F1A2 (Novo Nordisk, Bagsværd, Denmark) coupled to CNBr-activated Sepharose 4B (Pharmacia Biotech). The column was equilibrated with 50 mM Hepes, pH 7.5, containing 10 mM $CaCl_2$, 100 mM NaCl and 0.02% Triton X-100. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or [L305V]-FVII was transferred to a Ca²⁺-containing buffer. The yield of each step was followed by factor VII ELISA measurements and the purified protein was analysed by SDS-PAGE.

Example 4

Preparation of [F374P]-FVII.

BHK cells were transfected essentially as previously described (Thim et al. (1988) *Biochemistry* 27, 7785–7793; Persson and Nielsen (1996) *FEBS Lett*. 385, 241–243) to obtain expression of the variant [F374P]-FVII. The Factor VII variant was purified as follows:

Conditioned medium was loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein was accomplished by a gradient from 10 mM Tris, 50 mM NaCl, 0.1% Triton X-100, pH 8.0 to 10 mM Tris, 1 M NaCl, 5 mM CaCl₂, 0.1% Triton X-100, pH 7.5. The fractions containing [F374P]-FVII were pooled, 10 mM CaCl₂ was added, and applied to a 25-ml column containing monoclonal antibody F1A2 (Novo Nordisk, Bagsværd, Denmark) coupled to CNBr-activated Sepharose 4B (Pharmacia Biotech). The column was equilibrated with 50 mM Hepes, pH 7.5, containing 10 mM CaCl₂, 100 mM NaCl and 0.02% Triton X-100. After washing with equilibration buffer and equilibration buffer containing 2 M NaCl, bound material was eluted with equilibration buffer containing 10 mM EDTA instead of CaCl₂. Before use or storage, excess CaCl₂ over EDTA was added or [F374P]-FVII was transferred to a Ca²⁺-containing buffer. The yield of each step was followed by factor VII ELISA measurements and the purified protein was analysed by SDS-PAGE.

Example 5

Preparation of [L305I]-FVII and [L305T]-FVII

BHK cells are transfected essentially as previously described (Thim et al. (1988) *Biochemistry* 27, 7785–7793; Persson and Nielsen (1996) *FEBS Lett*. 385, 241–243) to obtain expression of the variant [L305I]-FVII or [L305T]-FVII. The Factor VII variant is purified as follows:

Conditioned medium is loaded onto a 25-ml column of Q Sepharose Fast Flow (Pharmacia Biotech) after addition of 5 mM EDTA, 0.1% Triton X-100 and 10 mM Tris, adjustment of pH to 8.0 and adjustment of the conductivity to 10–11 mS/cm by adding water. Elution of the protein is accomplished by a gradient from 10 mM Tris, 50 mM NaCl, 0.1% Triton X-100, pH 8.0 to 10 mM Tris, 1 M NaCl, 5 mM CaCl₂, 0.1% Triton X-100, pH 7.5. The fractions containing [L305I]-FVII or [L305T]-FVII are pooled, 10 mM CaCl₂ is added, and applied to a 25-ml column containing monoclonal antibody F1A2 (Novo Nordisk, Bagsværd, Denmark) coupled to CNBr-activated Sepharose 4B (Pharmacia Biotech). The column is equilibrated with 50 mM Hepes, pH 7.5, containing 10 mM CaCl₂, 100 mM NaCl and 0.02% Triton X-100. After washing with equilibration buffer and equilibration buffer containing 2 M NaCl, bound material is eluted with equilibration buffer containing 10 mM EDTA instead of CaCl₂. Before use or storage, excess CaCl₂ over EDTA is added or [L305I]-FVII or [L305T]-FVII are transferred to a Ca²⁺-containing buffer. The yield of each step is followed by factor VII ELISA measurements and the purified protein is analysed by SDS-PAGE.

Example 6

In vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM CaCl₂ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\ nm}$ Factor VIIa variant)/($A_{405\ nm}$ Factor VIIa wild-type).

Example 7

In vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl₂ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\ nm}$ Factor VIIa variant)/($A_{405\ nm}$ Factor VIIa wild-type).

Example 8

Relative Activities of FVIIa Variants Measured in the Assays Described in Examples 6 and 7

| Variant | Ratio in example 6 | Ratio in example 7 |
|---|---|---|
| L305V/M306D/D309S-FVIIa | 3.0 ± 0.1 | 6.3 ± 0.9 |
| L305V-FVIIa | 3.2 ± 0.2 | 3.3 ± 0.2 |
| F374P-FVIIa | 1.4 | <1 |
| wt-FVIIa | 1.0 | 1.0 |

SEQUENCE LISTING
(The amino acid sequence of native human coagulation Factor VII):
SEQ ID NO. 1

Ala-Asn-Ala-Phe-Leu-GLA-GLA-Leu-Arg-Pro-Gly-Ser-Leu-GLA-Arg-
                      5                  10                  15

GLA-Cys-Lys-GLA-GLA-Gln-Cys-Ser-Phe-GLA-GLA-Ala-Arg-GLA-Ile-Phe-Lys-Asp-Ala-GLA-Arg-
            20                  25                  30                  35

Thr-Lys-Leu-Phe-Trp-Ile-Ser-Tyr-Ser-Asp-Gly-Asp-Gln-Cys-Ala-Ser-Ser-Pro-
            40                  45                  50

Cys-Gln-Asn-Gly-Gly-Ser-Cys-Lys-Asp-Gln-Leu-Gln-Ser-Tyr-Ile-Cys-Phe-Cys-
55                  60                  65                  70

Leu-Pro-Ala-Phe-Glu-Gly-Arg-Asn-Cys-Glu-Thr-His-Lys-Asp-Asp-Gln-Leu-Ile-
            75                  80                  85                  90

Cys-Val-Asn-Glu-Asn-Gly-Gly-Cys-Glu-Gln-Tyr-Cys-Ser-Asp-His-Thr-Gly-Thr-
                95                  100                 105

Lys-Arg-Ser-Cys-Arg-Cys-His-Glu-Gly-Tyr-Ser-Leu-Leu-Ala-Asp-Gly-Val-Ser-
        110                 115                 120                 125

Cys-Thr-Pro-Thr-Val-Glu-Tyr-Pro-Cys-Gly-Lys-Ile-Pro-Ile-Leu-Glu-Lys-Arg-
            130                 135                 140

Asn-Ala-Ser-Lys-Pro-Gln-Gly-Arg-Ile-Val-Gly-Gly-Lys-Val-Cys-Pro-Lys-Gly-
145                 150                 155                 160

Glu-Cys-Pro-Trp-Gln-Val-Leu-Leu-Leu-Val-Asn-Gly-Ala-Gln-Leu-Cys-Gly-Gly-
        165                 170                 175                 180

Thr-Leu-Ile-Asn-Thr-Ile-Trp-Val-Val-Ser-Ala-Ala-His-Cys-Phe-Asp-Lys-Ile-
                185                 190                 195

Lys-Asn-Trp-Arg-Asn-Leu-Ile-Ala-Val-Leu-Gly-Glu-His-Asp-Leu-Ser-Glu-His-
        200                 205                 210                 215

Asp-Gly-Asp-Glu-Gln-Ser-Arg-Arg-Val-Ala-Gln-Val-Ile-Ile-Pro-Ser-Thr-Tyr-
            220                 225                 230

Val-Pro-Gly-Thr-Thr-Asn-His-Asp-Ile-Ala-Leu-Leu-Arg-Leu-His-Gln-Pro-Val-
235                 240                 245                 250

Val-Leu-Thr-Asp-His-Val-Val-Pro-Leu-Cys-Leu-Pro-Glu-Arg-Thr-Phe-Ser-Glu-
        255                 260                 265                 270

Arg-Thr-Leu-Ala-Phe-Val-Arg-Phe-Ser-Leu-Val-Ser-Gly-Trp-Gly-Gln-Leu-Leu-
                275                 280                 285

Asp-Arg-Gly-Ala-Thr-Ala-Leu-Glu-Leu-Met-Val-Leu-Asn-Val-Pro-Arg-Leu-Met-
    290                 295                 300                 305 306

Thr-Gln-Asp-Cys-Leu-Gln-Gln-Ser-Arg-Lys-Val-Gly-Asp-Ser-Pro-Asn-Ile-Thr-
                310                 315                 320

Glu-Tyr-Met-Phe-Cys-Ala-Gly-Tyr-Ser-Asp-Gly-Ser-Lys-Asp-Ser-Cys-Lys-Gly-
325                 330                 335                 340

Asp-Ser-Gly-Gly-Pro-His-Ala-Thr-His-Tyr-Arg-Gly-Thr-Trp-Tyr-Leu-Thr-Gly-
        345                 350                 355                 360

Ile-Val-Ser-Trp-Gly-Gln-Gly-Cys-Ala-Thr-Val-Gly-His-Phe-Gly-Val-Tyr-Thr-
                365                 370                 375

Arg-Val-Ser-Gln-Tyr-Ile-Glu-Trp-Leu-Gln-Lys-Leu-Met-Arg-Ser-Glu-Pro-Arg-
    380                 385                 390                 395

Pro-Gly-Val-Leu-Leu-Arg-Ala-Pro-Phe-Pro
            400                 405 406

FIG. 2 shows the region 300–322 of human coagulation Factor VII and
the corresponding region of homologous serine proteases:
(Region 300–322 of FVII):
SEQ ID NO 2

Leu-Asn-Val-Pro-Arg-Leu-Met-Thr-Gln-Asp-Cys-Leu-Gln-Gln-Ser-
1               5                   10                  15

-Arg-Lys-Val-Gly-Asp-Ser-Pro-Asn

-continued (Region of trypsin corresponding to region 300-322 of FVII):
SEQ ID NO 3
Leu-Lys-Ala-Pro-Ile-Leu-Asp-Asn-Ser-Ser-Cys-Lys-Ser-Ala-Tyr-Pro-Gly-Gln
1               5                   10                  15          18

(Region of thrombin corresponding to region 300-322 of FVII):
SEQ ID NO 4
Val-Asn-Leu-Pro-Ile-Val-Glu-Arg-Pro-Val-Cys-Lys-Asp-Ser-Thr-Arg-Ile-Arg
1               5                   10                  15          18

(Region of FXa corresponding to region 300-322 of FVII):
SEQ ID NO 5
Leu-Glu-Val-Pro-Tyr-Val-Asp-Arg-Asn-Ser-Cys-Lys-Leu-Ser-Ser-Ser-Phe-Ile
1               5                   10                  15          18

(Region 305-322 of FVII):
SEQ ID NO 6
Leu-Met-Thr-Gln-Asp-Cys-Leu-Gln-Gln-Ser-Arg-Lys-Val-Gly-Asp-Ser-Pro-Asn
1               5                   10                  15          18

(Region of trypsin corresponding to region 305-322 of FVII):
SEQ ID NO 7
Leu-Asp-Asn-Ser-Ser-Cys-Lys-Ser-Ala-Tyr-Pro-Gly-Gln
1               5                   10          13

(Region of thrombin corresponding to region 305-322 of FVII)
SEQ ID NO 8
Val-Glu-Arg-Pro-Val-Cys-Lys-Asp-Ser-Thr-Arg-Ile-Arg
1               5                   10          13

(Region of FXa corresponding to region 305-322 of FVII)
SEQ ID NO 9
Val-Asp-Arg-Asn-Ser-Cys-Lys-Leu-Ser-Ser-Ser-Phe-Ile
1               5                   10          13

(Region 300-312 of FVII):
SEQ ID NO 10
Leu-Asn-Val-Pro-Arg-Leu-Met-Thr-Gln-Asp-Cys-Leu-Gln
1               5                   10          13

(Region of trypsin corresponding to region 300-312 of FVII):
SEQ ID NO 11
Leu-Lys-Ala-Pro-Ile-Leu-Asp-Asn-Ser-Ser-Cys-Lys-Ser
1               5                   10          13

(Region of thrombin corresponding to region 300-312 of FVII):
SEQ ID NO 12
Val-Asn-Leu-Pro-Ile-Val-Glu-Arg-Pro-Val-Cys-Lys-Asp
1               5                   10          13

(Region of FXa corresponding to region 300-312 of FVII):
SEQ ID NO 13
Leu-Glu-Val-Pro-Tyr-Val-Asp-Arg-Asn-Ser-Cys-Lys-Leu
1               5                   10          13

(Region 305-312 of FVII):
SEQ ID NO 14
Leu-Met-Thr-Gln-Asp-Cys-Leu-Gln
1               5           8

(Region of trypsin corresponding to region 305-312 of FVII):
SEQ ID NO 15
Leu-Asp-Asn-Ser-Ser-Cys-Lys-Ser
1               5           8

(Region of thrombin corresponding to region 305-312 of EVI1):
SEQ ID NO 16
Val-Glu-Arg-Pro-Val-Cys-Lys-Asp
1               5           8

(Region of FXa corresponding to region 305-312 of FVII):
SEQ ID NO 17
Val-Asp-Arg-Asn-Ser-Cys-Lys-Leu
1               5           8

(DNA primer for preparation of [L305V]-FVII):
5'-CGT GCC CCG GGT GAT GAC CCA GGA C-3'           SEQ ID NO 18

-continued (DNA primer for preparation of [L305V]-FVII):
5'-GTC CTG GGT CAT CAC CCG GGG CAC G-3'    SEQ ID NO 19

(DNA primer for preparation of [M306D/D309S]-FVII):
5'-TCT AGA TAC CCA GTC TTG CCT GCA GCA GTC ACG AAA-3'    SEQ ID NO 20

(DNA primer for preparation of [M306D/D309S]-FVII):
5'-TTC CGT GAC TGC TGC AGG CAA GAC TGG GTA TCT AGA-3'    SEQ ID NO 21

(DNA primer for preparation of [F374P]-FVII):
5'-CCG TGG GCC ACC TGG GGT GTA CAC C-3'    SEQ ID NO 22

(DNA primer for preparation of [F374P]-FVII):
5'-GGT GTA CAC CCC AGG GTG GCC CAC GG-3'    SEQ ID NO 23

(DNA primer for preparation of [L305I]-FVII:
5'-CCT CAA CGT GCC CCG GAT CAT GAC CCA GGA C-3'    SEQ ID NO 24

(DNA primer for preparation of [L305I]-FVII:
5'-GTC CTG GGT CAT GAT CCG GGG CAC GTT GAG G-3'    SEQ ID NO 25

(DNA primer for preparation of [L305T]-FVII):
5'-CCT CAA CGT GCC CCG GAC GAT GAC CCA GGA C-3'    SEQ ID NO 26

(DNA primer for preparation of [L305T]-FVII):
5'-GTC CTG GGT CAT CGT CCG GGG CAC GTT GAG G-3'    SEQ ID NO 27

---

What is claimed is:

1. A human coagulation Factor VII variant comprising a substitution of the Leu position 305 of SEQ ID NO 1 with an amino acid residue selected from the group consisting of Val, Ile, Met, Phe, Trp, Pro, Gly, Ser, Thr, Cys, Tyr, Asn, Glu, Lys, Arg, His, Asp and Gln, wherein the ratio between the activity of the variant and the activity of native Factor VII polypeptide having a sequence shown in SEQ ID NO 1 is at least about 1.25 when tested in an in vitro hydrolysis assay.

2. A Factor VII variant as defined in claim 1, wherein the substituted amino acid is selected from the group consisting of Val, Tyr, and Ile.

3. A Factor VII variant as defined in claim 1, further comprising one or more substitutions selected from the group consisting of (i) position 274; (ii) any of positions 300–304; (iii) any of positions 306–312; and (iv) combinations of any of the foregoing.

4. A Factor VII variant as clothed in claim 3, wherein the second substitution is at position 274.

5. A Factor VII variant as defined in claim 3, wherein the second substitution is at any of positions 300–304.

6. A Factor VII variant as defined in claim 3, wherein the second substitution is at any of positions 306–312.

7. A Factor VII variant as described in claim 1, wherein the Leu residue in position 305 is the only amino acid residue that has been replaced relative to the sequence of SEQ ID NO:1.

8. A human coagulation Factor VII variant, comprising a substitution of the Leu in position 305 of SEQ ID NO 1 with Val.

9. A human coagulation Factor VII variant, comprising a first substitution of the Leu in position 305 of SEQ ID NO 1 with Val and one or more substitutions selected from the group consisting of: (i) substitution of Ala 274 with Met, Leu, Lys, or Arg; (ii) substitution of Arg 304 with Tyr, Phe, Leu, or Met; (iii) substitution of Met 306 with Asp or Asn; (iv) substitution of Asp 309 with Ser or Thr, and (iv) combinations of any of the foregoing.

10. A Factor VII variant as defined in claim 1, wherein the ratio is at least about 2.0.

11. A Factor VII variant as defined in claim 1, wherein the ratio is at least about 4.0.

12. A human coagulation Factor VII variant comprising a substitution of the Leu in position 305 of SEQ ID NO 1 with an amino acid residue selected from the group consisting of Val, Tyr, and Ile, wherein the ratio between the activity of the variant and the activity of native Factor VII polypeptide having a sequence shown in SEQ ID NO 1 is at least about 1.25 when tested in an in vitro hydrolysis assay.

13. A pharmaceutical composition comprising (i) a human coagulation Factor VII variant as defined in claim 1 and (ii) a pharmaceutically acceptable carrier or excipient.

14. A pharmaceutical composition comprising (i) a human coagulation Factor VII variant as defined in claim 2 and (ii) a pharmaceutically acceptable carrier or excipient.

15. A pharmaceutical composition comprising (i) a human coagulation Factor VII variant as defined in claim 3 and (ii) a pharmaceutically acceptable carrier or excipient.

16. A pharmaceutical composition comprising (i) a human coagulation Factor VII variant as defined in claim 7 and (ii) a pharmaceutically acceptable carrier or excipient.

17. A pharmaceutical composition comprising (i) a human coagulation Factor VII variant as defined in claim 8 and (ii) a pharmaceutically acceptable carrier or excipient.

18. A method for the treatment of bleeding episodes in a subject or for the enhancement of the normal haemostatic system, the method comprising administering to a subject need of such treatment a therapeutically or prophylactically effective amount of a human coagulation Factor VII variant as defined in claim 1.

19. A method for the treatment of bleeding episodes in a subject or for the enhancement of the normal haemostatic system, the method comprising administering to a subject need of such treatment a therapeutically or prophylactically effective amount of a human coagulation Factor VII variant as defined in claim 8.

* * * * *

SEQUENCE LISTING

<160> NUMBER OF SEQ ID NOS: 27

<210> SEQ ID NO 1
<211> LENGTH: 426
<212> TYPE: PRT
<213> ORGANISM: Human

<400> SEQUENCE: 1

Ala Asn Ala Phe Leu Gly Leu Ala Gly Leu Ala Leu Arg Pro Gly Ser
 1               5                  10                  15

Leu Gly Leu Ala Arg Gly Leu Ala Cys Lys Gly Leu Ala Gly Leu Ala
            20                  25                  30

Gln Cys Ser Phe Gly Leu Ala Gly Leu Ala Ala Arg Gly Leu Ala Ile
        35                  40                  45

Phe Lys Asp Ala Gly Leu Ala Arg Thr Lys Leu Phe Trp Ile Ser Tyr
    50                  55                  60

Ser Asp Gly Asp Gln Cys Ala Ser Ser Pro Cys Gln Asn Gly Ser
65                  70                  75                  80

Cys Lys Asp Gln Leu Gln Ser Tyr Ile Cys Phe Cys Leu Pro Ala Phe
                85                  90                  95

Glu Gly Arg Asn Cys Glu Thr His Lys Asp Asp Gln Leu Ile Cys Val
            100                 105                 110

Asn Glu Asn Gly Gly Cys Glu Gln Tyr Cys Ser Asp His Thr Gly Thr
        115                 120                 125

Lys Arg Ser Cys Arg Cys His Glu Gly Tyr Ser Leu Leu Ala Asp Gly
    130                 135                 140

Val Ser Cys Thr Pro Thr Val Glu Tyr Pro Cys Gly Lys Ile Pro Ile
145                 150                 155                 160

Leu Glu Lys Arg Asn Ala Ser Lys Pro Gln Gly Arg Ile Val Gly Gly
                165                 170                 175

Lys Val Cys Pro Lys Gly Glu Cys Pro Trp Gln Val Leu Leu Leu Val
            180                 185                 190

Asn Gly Ala Gln Leu Cys Gly Gly Thr Leu Ile Asn Thr Ile Trp Val

-continued

```
                195                 200                 205
Val Ser Ala Ala His Cys Phe Asp Lys Ile Lys Asn Trp Arg Asn Leu
    210                 215                 220

Ile Ala Val Leu Gly Glu His Asp Leu Ser Glu His Asp Gly Asp Glu
225                 230                 235                 240

Gln Ser Arg Arg Val Ala Gln Val Ile Ile Pro Ser Thr Tyr Val Pro
                245                 250                 255

Gly Thr Thr Asn His Asp Ile Ala Leu Leu Arg Leu His Gln Pro Val
            260                 265                 270

Val Leu Thr Asp His Val Val Pro Leu Cys Leu Pro Glu Arg Thr Phe
        275                 280                 285

Ser Glu Arg Thr Leu Ala Phe Val Arg Phe Ser Leu Val Ser Gly Trp
    290                 295                 300

Gly Gln Leu Leu Asp Arg Gly Ala Thr Ala Leu Glu Leu Met Val Leu
305                 310                 315                 320

Asn Val Pro Arg Leu Met Thr Gln Asp Cys Leu Gln Gln Ser Arg Lys
                325                 330                 335

Val Gly Asp Ser Pro Asn Ile Thr Glu Tyr Met Phe Cys Ala Gly Tyr
            340                 345                 350

Ser Asp Gly Ser Lys Asp Ser Cys Lys Gly Asp Ser Gly Gly Pro His
        355                 360                 365

Ala Thr His Tyr Arg Gly Thr Trp Tyr Leu Thr Gly Ile Val Ser Trp
    370                 375                 380

Gly Gln Gly Cys Ala Thr Val Gly His Phe Gly Val Tyr Thr Arg Val
385                 390                 395                 400

Ser Gln Tyr Ile Glu Trp Leu Gln Lys Leu Met Arg Ser Glu Pro Arg
                405                 410                 415

Pro Gly Val Leu Leu Arg Ala Pro Phe Pro
            420                 425

<210> SEQ ID NO 2
<211> LENGTH: 23
<212> TYPE: PRT
<213> ORGANISM: Human

<400> SEQUENCE: 2

Leu Asn Val Pro Arg Leu Met Thr Gln Asp Cys Leu Gln Gln Ser Arg
1               5                   10                  15

Lys Val Gly Asp Ser Pro Asn
            20

<210> SEQ ID NO 3
<211> LENGTH: 18
<212> TYPE: PRT
<213> ORGANISM: Human

<400> SEQUENCE: 3

Leu Lys Ala Pro Ile Leu Asp Asn Ser Ser Cys Lys Ser Ala Tyr Pro
1               5                   10                  15

Gly Gln

<210> SEQ ID NO 4
<211> LENGTH: 18
<212> TYPE: PRT
<213> ORGANISM: Human

<400> SEQUENCE: 4
```

```
Val Asn Leu Pro Ile Val Glu Arg Pro Val Cys Lys Asp Ser Thr Arg
 1               5                  10                  15

Ile Arg

<210> SEQ ID NO 5
<211> LENGTH: 18
<212> TYPE: PRT
<213> ORGANISM: Human

<400> SEQUENCE: 5

Leu Glu Val Pro Tyr Val Asp Arg Asn Ser Cys Lys Leu Ser Ser Ser
 1               5                  10                  15

Phe Ile

<210> SEQ ID NO 6
<211> LENGTH: 18
<212> TYPE: PRT
<213> ORGANISM: Human

<400> SEQUENCE: 6

Leu Met Thr Gln Asp Cys Leu Gln Gln Ser Arg Lys Val Gly Asp Ser
 1               5                  10                  15

Pro Asn

<210> SEQ ID NO 7
<211> LENGTH: 13
<212> TYPE: PRT
<213> ORGANISM: Human

<400> SEQUENCE: 7

Leu Asp Asn Ser Ser Cys Lys Ser Ala Tyr Pro Gly Gln
 1               5                  10

<210> SEQ ID NO 8
<211> LENGTH: 13
<212> TYPE: PRT
<213> ORGANISM: Human

<400> SEQUENCE: 8

Val Glu Arg Pro Val Cys Lys Asp Ser Thr Arg Ile Arg
 1               5                  10

<210> SEQ ID NO 9
<211> LENGTH: 13
<212> TYPE: PRT
<213> ORGANISM: Human

<400> SEQUENCE: 9

Val Asp Arg Asn Ser Cys Lys Leu Ser Ser Ser Phe Ile
 1               5                  10

<210> SEQ ID NO 10
<211> LENGTH: 13
<212> TYPE: PRT
<213> ORGANISM: Human

<400> SEQUENCE: 10

Leu Asn Val Pro Arg Leu Met Thr Gln Asp Cys Leu Gln
 1               5                  10

<210> SEQ ID NO 11
<211> LENGTH: 13
<212> TYPE: PRT
```

<213> ORGANISM: Human

<400> SEQUENCE: 11

Leu Lys Ala Pro Ile Leu Asp Asn Ser Ser Cys Lys Ser
1               5                   10

<210> SEQ ID NO 12
<211> LENGTH: 13
<212> TYPE: PRT
<213> ORGANISM: Human

<400> SEQUENCE: 12

Val Asn Leu Pro Ile Val Glu Arg Pro Val Cys Lys Asp
1               5                   10

<210> SEQ ID NO 13
<211> LENGTH: 13
<212> TYPE: PRT
<213> ORGANISM: Human

<400> SEQUENCE: 13

Leu Glu Val Pro Tyr Val Asp Arg Asn Ser Cys Lys Leu
1               5                   10

<210> SEQ ID NO 14
<211> LENGTH: 8
<212> TYPE: PRT
<213> ORGANISM: Human

<400> SEQUENCE: 14

Leu Met Thr Gln Asp Cys Leu Gln
1               5

<210> SEQ ID NO 15
<211> LENGTH: 8
<212> TYPE: PRT
<213> ORGANISM: Human

<400> SEQUENCE: 15

Leu Asp Asn Ser Ser Cys Lys Ser
1               5

<210> SEQ ID NO 16
<211> LENGTH: 8
<212> TYPE: PRT
<213> ORGANISM: Human

<400> SEQUENCE: 16

Val Glu Arg Pro Val Cys Lys Asp
1               5

<210> SEQ ID NO 17
<211> LENGTH: 8
<212> TYPE: PRT
<213> ORGANISM: Human

<400> SEQUENCE: 17

Val Asp Arg Asn Ser Cys Lys Leu
1               5

<210> SEQ ID NO 18
<211> LENGTH: 25
<212> TYPE: DNA
<213> ORGANISM: Artificial Sequence
<220> FEATURE:

<223> OTHER INFORMATION: Synthetic

<400> SEQUENCE: 18
cgtgccccgg gtgatgaccc aggac    25

<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
gtcctgggtc atcacccggg gcacg    25

<210> SEQ ID NO 20
<211> LENGTH: 36
<212> TYPE: DNA
<213> ORGANISM: Artificial Sequence
<220> FEATURE:
<223> OTHER INFORMATION: Synthetic

<400> SEQUENCE: 20
tctagatacc cagtcttgcc tgcagcagtc acggaa    36

<210> SEQ ID NO 21
<211> LENGTH: 36
<212> TYPE: DNA
<213> ORGANISM: Artificial Sequence
<220> FEATURE:
<223> OTHER INFORMATION: Synthetic

<400> SEQUENCE: 21
ttccgtgact gctgcaggca agactgggta tctaga    36

<210> SEQ ID NO 22
<211> LENGTH: 26
<212> TYPE: DNA
<213> ORGANISM: Artificial Sequence
<220> FEATURE:
<223> OTHER INFORMATION: Synthetic

<400> SEQUENCE: 22
ccgtgggcca ccctggggtg tacacc    26

<210> SEQ ID NO 23
<211> LENGTH: 26
<212> TYPE: DNA
<213> ORGANISM: Artificial Sequence
<220> FEATURE:
<223> OTHER INFORMATION: Synthetic

<400> SEQUENCE: 23
ggtgtacacc ccagggtggc ccacgg    26

<210> SEQ ID NO 24
<211> LENGTH: 31
<212> TYPE: DNA
<213> ORGANISM: Artificial Sequence
<220> FEATURE:
<223> OTHER INFORMATION: Synthetic

<400> SEQUENCE: 24
cctcaacgtg ccccggatca tgacccagga c    31

```
-continued

<210> SEQ ID NO 25
<211> LENGTH: 31
<212> TYPE: DNA
<213> ORGANISM: Artificial Sequence
<220> FEATURE:
<223> OTHER INFORMATION: Synthetic

<400> SEQUENCE: 25
gtcctgggtc atgatccggg gcacgttgag g                              31

<210> SEQ ID NO 26
<211> LENGTH: 31
<212> TYPE: DNA
<213> ORGANISM: Artificial Sequence
<220> FEATURE:
<223> OTHER INFORMATION: Synthetic

<400> SEQUENCE: 26
cctcaacgtg ccccggacga tgacccagga c                              31

<210> SEQ ID NO 27
<211> LENGTH: 31
<212> TYPE: DNA
<213> ORGANISM: Artificial Sequence
<220> FEATURE:
<223> OTHER INFORMATION: Synthetic

<400> SEQUENCE: 27
gtcctgggtc atcgtccggg gcacgttgag g                              31
```